United States Patent [19]

Guibert

[11] E Patent Number: Re. 31,765

[45] Reissued Date of Patent: Dec. 11, 1984

[54] COUNTER-TOP OVEN

[75] Inventor: Raul Guibert, Los Angeles, Calif.

[73] Assignee: Sunset Ltd., Los Angeles, Calif.

[21] Appl. No.: 561,512

[22] Filed: Dec. 14, 1983

Related U.S. Patent Documents

Reissue of:

[64] Patent No.: 4,374,319
Issued: Feb. 15, 1983
Appl. No.: 221,206
Filed: Dec. 30, 1980

U.S. Applications:

[63] Continuation-in-part of Ser. No. 97,787, Nov. 27, 1979, Pat. No. 4,307,286.

[51] Int. Cl.[3] ..... A21B 1/22; F27D 11/02

[52] U.S. Cl. ..... 219/400; 126/21 A; 219/370; 219/385; 219/405; 219/411

[58] Field of Search ..... 219/367, 369, 370, 376, 219/385, 386, 396, 400, 405, 411; 99/427, 480; 126/21 A, 261

[56] References Cited

U.S. PATENT DOCUMENTS

| | | | |
|---|---|---|---|
| 3,548,153 | 12/1970 | Kells | 219/400 |
| 4,029,463 | 6/1977 | Johansson et al. | 432/25 |
| 4,132,216 | 1/1979 | Guibert | 126/261 |
| 4,283,614 | 8/1981 | Tanaka et al. | 219/10.55 R |
| 4,295,419 | 10/1981 | Langhammer | 99/427 |
| 4,307,286 | 12/1981 | Guibert | 219/400 |
| 4,374,319 | 2/1983 | Guibert | 219/400 |

FOREIGN PATENT DOCUMENTS

| | | | |
|---|---|---|---|
| 2334285 | 1/1975 | Fed. Rep. of Germany | 126/21 A |

*Primary Examiner*—Volodymyr Y. Mayewsky
*Attorney, Agent, or Firm*—Michael Ebert

[57] ABSTRACT

A counter-top oven adapted to effect low-temperature cooking of food at a relatively rapid rate whereby food nutrients and other valuable constituents are preserved. The oven includes a food-receiving compartment having a perforated wall and means to heat air to a temperature well above the cooking temperature of the food and to force the heated air through the perforations to cause the air to flow at high velocity through the compartment in heat-exchange relation with the food. This air flow is periodically interrupted to produce hot air pulses having no-flow intervals therebetween to create a laminar heat transfer pattern in which heat from the outer layer of the body of food is transferred to the intermediate layers and the core thereof in these intervals to a degree preventing the temperature of the outer layer from rising substantially above cooking temperature despite the much higher temperature of the air pulses whereby the intermediate layers and the core are caused to reach the cooking temperature in a relatively short period.

15 Claims, 4 Drawing Figures

COUNTER-TOP OVEN

Matter enclosed in heavy brackets [ ] appears in the original patent but forms no part of this reissue specification; matter printed in italics indicates the additions made by reissue.

RELATED APPLICATION

This application is a continuation-in-part of my copending application Ser. No. 97,787 filed Nov. 27, 1979 entitled "Pulsating Hot Air Heat-Up System" now U.S. Pat. No. 4,307,286, which in turn relates back to earlier-filed applications which are now U.S. Pat. Nos. 4,132,216 and 4,122,916, the entire disclosures of which are hereby incorporated by reference in the instant application.

BACKGROUND OF INVENTION

This invention relates generally to counter-top ovens for domestic or commercial use, and in particular to an oven capable of carrying out all of the usual food baking, defrosting and other cooking functions of ovens of the conventional type and also adapted to effect low-temperature cooking of food at a much faster rate than standard ovens.

The term "counter-top oven," as used herein, is intended to apply to any oven which is sufficiently compact to be placed on top of a table or counter, but the term is not limited to ovens so placed, and the heat transfer principles involved are applicable to any food cooking oven regardless of its size.

A multi-function counter-top electrical oven such as the Proctor-Silex Meal Maker II manufactured by SCM Corporation of Baltimore, Md., is adapted to bake, broil and slow-cook food products and to carry out other food heating functions. Ovens of this type are provided with thermostatically-controlled resistance heater elements operating in conjunction with an adjustable timer to generate oven heat at a predetermined level for a preset time period appropriate to the nature of the intended cooking action, such as baking or broiling. The "Versatron Electronic Countertop Oven" marketed by GE is further adapted to top brown as well as to cook food, the necessary high temperatures for this function being produced by quartz tube heating elements.

In order to bring about a uniform distribution of heat and thereby avoid hot spots that would otherwise burn the food, the oven disclosed in U.S. Pat. No. 3,828,760 of Faber et al. is provided with a forced-air convection system in which the heated air is caused to assume a cyclonic turbulent pattern. This oven is intended for broiling, roasting and baking and may be used for defrosting as well.

The boiling point of water is 212° F., whereas food typically undergoes cooking when its internal temperature is below this boiling point; that is, at about 140° to 200° F. Yet the common practice with conventional ovens is to establish an oven temperature that runs as high as 500° F. Thus in the "Oven Guide" attached to the "Versatron" oven above-identified, the oven temperature for cooking frozen dinners is given as 425° F., for baking biscuits as 450° F., and for keeping food warm or for reheating pre-cooked food as 300° F.

The reason why in a conventional oven, the interior temperature is so much above the temperature at which food cooks is that the rate of heat transfer between the hot oven atmosphere and the body of the food is high only when the temperature differential therebetween is great.

If, therefore, the food placed in the oven is initially at a temperature of 70° F. and the oven temperature is held at 220° F., then as the body of food becomes warmer and its surface temperature reaches, say, 150° F., the rate of heat transfer becomes increasingly sluggish, so that it would literally take many hours to fully cook the food.

On the other hand, when the temperature differential is great, say, with an oven atmosphere at a temperature of 400° F. and a food surface temperature initially at 70° F., at no time in the course of cooking is the temperature differential small. The cooking rate is therefore quite fast even as the body temperature approaches the cooking temperature. However, with these conventional ovens in which a large heat differential exists, there is always the danger of overcooking or burning the food.

Because the outer layer of the food body is in direct heat transfer relation with the oven atmosphere whereas the intermediate layers and core are, by their very nature, thermally-insulated therefrom by the outer layer, in order to heat up and cook the intermediate layers and core, it is necessary to somewhat overcook or possibly burn the outer layer. Hence if the food is withdrawn from the oven when the outer layer appears to be adequately cooked, the food body may then be insufficiently cooked at the core and at the intermediate layers.

The deleterious effects of high-temperature cooking on food is well recognized, for such cooking is destructive of nutrients, vitamins and valuable soluble constitutents, and tends to rob food of its taste and flavor. The preferable practice is, therefore, to cook food at a low temperature, this being traditionally accomplished with an oven temperature not much higher than the cooking temperature of the food.

With conventional low-temperature cooking, the nutrients and other valuable constituents are preserved and the food is much more flavorsome than when subjected to high temperature cooking. But with counter-top ovens of the type heretofore known, a heavy penalty is paid when operating the oven in the low-temperature mode, for the resultant small heat differential is such that it takes as much as 8 hours or longer to cook the food.

This explains why in the "Use and Care" manual published for the Proctor-Silex oven, low temperature cooking is referred to therein as "slow cooking" or as a "low temperature slow cook;" for prior to the present invention, low temperature cooking was invariably very slow. Hence while the advantages gained by low-temperature cooking are appreciated by most consumers, many of them simply cannot afford the time it takes and therefore use their counter-top ovens only for high-temperature fast cooking. This problem is especially bothersome when dealing with pre-cooked frozen meals.

Another drawback of conventional ovens, particularly those capable of low-temperature slow cooking, is that because these ovens are usually provided with uninsulated metal housings that are thermally conductive and discharge heat into the room, much of the energy required to carry out cooking is wasted during the prolonged cooking period. Also, an oven having a high housing temperature represents a hazard, for it can seriously burn an individual who touches the housing.

SUMMARY OF THE INVENTION

In view of the foregoing, the main object of this invention is to provide a counter-top oven adapted to carry out low-temperature cooking of food more efficiently and at a much more rapid rate than ovens of the type heretofore known. An oven in accordance with the invention is also capable of rethermalizing precooked meals without cooking.

Also an object of the invention is to provide an oven of the above-type capable of operating in any desired mode for broiling, baking and otherwise cooking food without however overcooking or burning the food.

A significant feature of the present invention is that the oven acts to heat the interior atmosphere thereof to a high temperature level comparable to that produced by conventional ovens in order to promote rapid heat transfer, yet it creates a heat transfer pattern that is conducive to proper cooking without deleterious effects.

Still another object of the invention is to provide an oven of the above-type which includes a browning facility acting to effectively and uniformly brown the outer surface of the food without however burning any region on the surface thereof.

Yet another object of the invention is to provide an oven which has relatively low heat leakage losses and which may be manufactured and sold at low cost.

Briefly stated, these objects are attained in a counter-top oven whose housing or case has supported therein a food-receiving compartment in a manner defining air spaces between the case and compartment walls, one of which is perforated. Disposed in one of these air spaces are means to heat the air therein to a temperature well above the cooking temperature of the food, and to create a pressure differential between the air in the air spaces and the air in the compartment which function to force the heated air through the perforations and causes the heated air to flow through the compartment at high velocity in heat transfer relation to the food therein, the resultant forced-convection producing a rapid heat exchange between the food or a food container and the air.

Means are provided to periodically interrupt the forced air flow to generate within the compartment hot air pulses having no-flow intervals therebetween in a manner creating a laminar heat transfer pattern in which heat acquired by the outer layer of the food body is transferred in these intervals to the intermediate layers and the core of the body, causing the outer layer to go down in temperature during these intervals to a degree preventing the temperature of the outer layer from rising substantially above its cooking temperature despite the much higher temperature of the air pulses. In this way, intermediate layers and the core of the food body are caused to reach the cooking temperature in a relatively short period, and low-temperature cooking is effected rapidly in an oven whose atmosphere is heated to a much higher temperature. At no time is the heat differential between the outer layer of the food and the hot air low; hence the rate of heat transfer is always high.

To effect browning without burning, the compartment may also include a bank of quartz infrared heater elements that are sequentially and cyclically energized to cause the heat rays therefrom to sweep repeatedly across the surface of the food body so that at no time is any region on this surface permitted to reach a burning temperature level.

OUTLINE OF DRAWINGS

For a better understanding of the invention as well as other objects and further features thereof, reference is made to the following detailed description to be read in conjunction with the accompanying drawings, wherein.

DESCRIPTION OF INVENTION

First Embodiment

Figure 1:
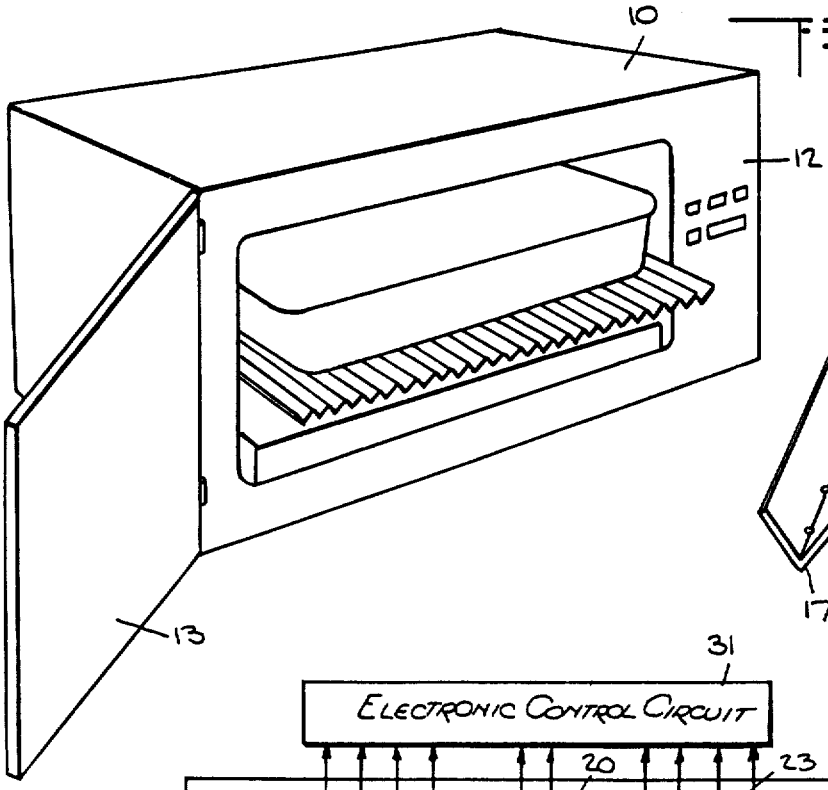
FIG. 1 is a perspective view of a first preferred embodiment of a counter-top oven in accordance with the invention.
Figure 3:
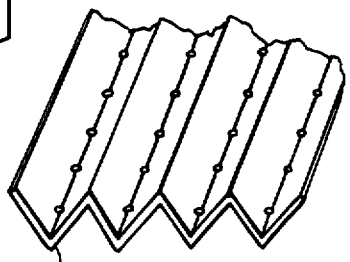
FIG. 3 is a separate and fragmentary view of the sliding shelf included in the oven.
Figure 2:
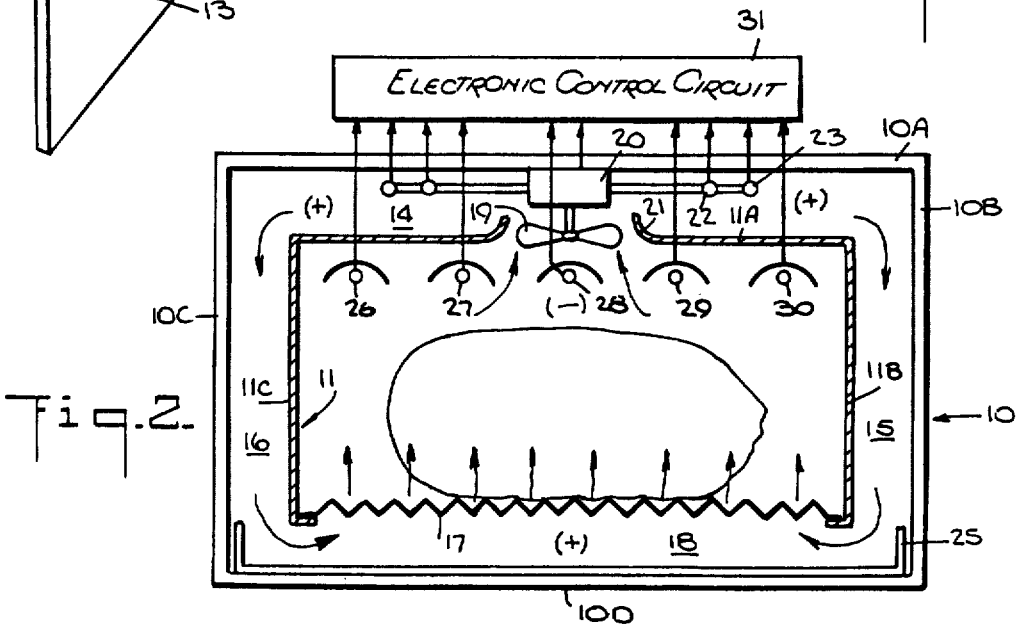
FIG. 2 is a longitudinal section taken through the oven, the section being somewhat schematic in form.

Referring now to FIGS. 1 to 3, an oven in accordance with the invention includes a box-like housing or case 10 having supported therein a food-receiving compartment 11 provided with an open front, access to the compartment being through the front of the case. Case 10 includes a control panel 12 provided with control switches as well as time and temperature-setting knobs and indicators. The case also includes a hinged door 13 which, when shut, closes the compartment, or an air curtain may be used for the same purpose.

Case 10, preferably fabricated of thermally-insulated walls, includes top wall 10A, side walls 10B and 10C and base 10D. Upper wall 11A and side walls 11B and 11C are spaced from their correspondingly-lettered case walls to define an upper air space 14 and side air spaces 15 and 16. The bottom wall of compartment 11 is constituted by a sliding shelf 17 which is spaced above base 10D of the case to define a bottom air space 18. Shelf 17 serves to support the food load and after the food is cooked may be slid out of the oven to make the food available to the user.

Mounted within upper air space 14 at the center thereof is a suction fan 19 drive at high speed by a motor 20. The fan is placed just above an upper wall port 21 so that when the fan is operated, it draws air from compartment 11. The air so drawn is blown by fan 19 through electric resistance heater elements in the form of coils 22 and 23 surrounding motor 20. In practice these coils may have different wattage ratings so as to selectively provide three heat levels, the first level being produced by energizing only coil 22, the second by energizing only coil 23, and the third by energizing both coils concurrently.

The heated air is blown down side air spaces 15 and 16 into bottom space 17, the air then entering the compartment through holes in shelf 17. Shelf 17, as shown separately in FIG. 3, is of corrugated or fluted construction, so that the food 24 placed therein rests on the peaks of the flutes above the troughs. The troughs of the shelf have rows of perforations thereon to admit air. Hence air enters the compartment through perforations in the shelf which forms the bottom wall of the compartment.

Below shelf 17 is a pull-out pan 25 which acts to receive whatever drippings come through the shelf from the food should the food not be in a sealed container. One may put water in the pan to collect hot grease that otherwise might drip onto the base of the case.

Mounted within compartment 11 above the food load therein is a bank of quartz heater elements 26, 27, 28, 29 and 30. Each element is placed within a reflector projecting heat rays from the element to the surface of the food to be browned, the rays being confined within a sector determined by the geometry of the reflector. The browning arrangement is such that if all of elements 26 to 30 were on simultaneously, the entire surface of the food in the compartment would be radiated all at once. But if this were to be done, there is a danger that some regions in the surface would reach a temperature above the browning state and therefore burn.

Hence quartz heater elements 26 to 30 are operatively connected to an electronic control circuit 31 which acts to selectively energize these elements in a manner to be later explained in the "Operation" section to follow. Control circuit 31 also acts to govern the operation of fan motor 20 and heater elements 22 and 23. The switches indicators and control knobs associated with circuit 31 appear on control panel 12. In practice a quartz glass slide plate may be placed in the compartment below the bank of quartz heaters to protect these heaters from food splatter. When the food is in a covered tray, the cover material should be permeable to rays emanating from the quartz heaters.

OPERATION

When fan 19 is activated to draw air from compartment 11 containing a food load 24, it creates a negative pressure in this compartment and a positive pressure in the surrounding air spaces 14, 15, 16 and 18. The resultant pressure differential forces air through the perforations in shelf 17 to produce high velocity air streams flowing throughout the compartment.

When heaters 22 and 23 are on, air drawn from the compartment by fan 19 is heated in air space 14 to a high temperature so that it is hot air that is forced through the shelf perforations. Heat is extracted from the hot air flowing through compartment 11 by food load 24, the air then being returned to port 21. Hence the air within the oven is circulated in a continuous flow loop which runs through a heating station external to the compartment.

In practice, the wattages of heaters 22 and 23 are such that when both these thermostatically-controlled elements are energized, the interior air in the oven is heated to a temperature level well above the cooking temperature of the food to be cooked. The actual level of temperature is settable by the oven controls and it may be comparable to any of those listed in the "Versatron" oven guide previously mentioned. Obviously, with an oven temperature at a high level, low-temperature cooking is ordinarily impossible. In practice, after the food is cooked, it may be held at a serving temperature level by energizing only the low wattage heater 22.

In order to carry out rapid yet low-temperature cooking, electronic control circuit 31 operates to switch both fan motor 20 and heater elements 22 and 23 on and off periodically at a rate, say, of one-half minute "on" followed by one-half minute "off" in each cycle. Thus instead of a continuous stream of hot air blowing at high velocity through the compartment, the flow is constituted by hot air pulses having distinct no-flow intervals therebetween.

For purposes of thermal analysis, a body of food may be said to consist of a core, an outer layer abjoining its surface and intermediate layers between the core and the outer layer. When food is cooked in a hot air oven, the outer layer first heats up continuously to a high level, for it is in direct heat exchange relation with the hot air. Heat is then transferred from the heated outer layer to the intermediate layers and from these layers to the core, the core inevitably being the last to cook.

The pulsatory heat wave produced in an oven in accordance with the invention is arranged to create a laminar transfer pattern in which the temperature acquired by the outer layer of the food body from hot air pulses whose temperature is much above the cooking temperature of the food, is never sufficient to bring the outer layer to a temperature substantially above the cooking temperature; for in the no-flow intervals, heat is leaked from the outer layer to the intermediate layers and from the intermediate layers to the core.

In this way, the outer layer during the no-flow intervals gives up heat to the intermediate layers, and the resultant reduction in outer layer temperature prevents it from rising in temperature substantially above the cooking temperature. In other words, even though the hot air pulses in the oven are at a high temperature level, cooking is nevertheless carried out at low-temperature; for no part of the food body is ever heated above the low-temperature cooking level.

While the pulsatory wave is produced in the oven shown in FIG. 1 by turning both the heaters and fan "on" and "off," in practice these elements may be kept "on" at all times, and a vane or other air flow control means of the type disclosed in the above-identified copending application may be used to periodically interrupt the flow of hot air through the compartment.

Control circuit 31, when the food is to be browned after being low-temperature cooked, acts to cyclically energize the quartz heater elements 26 to 30 in sequence so that only one element is on at any time. In this way the heat radiated from these elements effectively sweeps across the surface of the food body and no region thereof is even exposed to radiation for more than a brief period in the course of each sweep.

It is to be understood that the oven operation in the pulsatory low-temperature cooking mode is but one of several possible oven modes. Thus cooking, reheating or defrosting of food may be carried out in the oven at pre-set high temperature levels for adjustable timed periods as in a conventional oven, without a pulsatory action and, of course, without the low-temperature cooking advantages thereof. However, in broiling meat and in carrying out other operations, the operator may prefer the advantages of low-temperature cooking, being also able to form a crust by somewhat overcooking or even burning the food surfaces as in a conventional oven.

An advantage of an oven in accordance with the invention, as against commercially available counter top ovens even when it operates in a non-pulsatory mode, is that it provides high velocity forced air convection heating which promotes a rapid heat up.

SECOND EMBODIMENT

Figure 4:
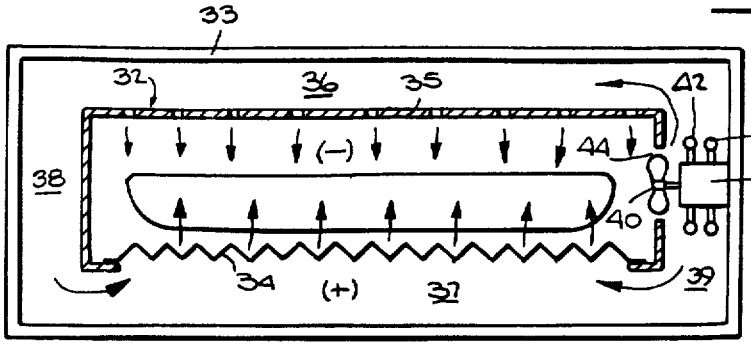
FIG. 4 is a section taken through a second embodiment of the oven.

In the counter-top oven shown in FIG. 4, the compartment 32 supported within a case 33 is provided with a bottom wall in the form of a perforated slidable shelf 34 comparable to shelf 17 in FIG. 2, and also with a perforated top wall 35. Compartment 32 is supported within the case to define between the walls of the compartment and the walls of the case, upper and lower air spaces 36 and 37, and left and right side air spaces 38 and 39.

Mounted in side air space 39 is a fan 40 driven by a motor 41 which draws air from the compartment through a side port 44. The air is heated by heater element 42 and 43 before being blown into air spaces 36 and 37. As a consequence, the air in the compartment is under negative pressure and that in the air spaces surrounding the compartment is under positive pressure. The resultant pressure differential forces air through the perforations in the upper wall 35 and in the lower shelf wall 34, so that the high velocity air flow through the compartment is in opposing directions to bring about a uniform distribution therein of hot air.

The hot air flow stream thereby produced through the compartment which houses a sealed tray of food to be cooked is periodically pulsed in the manner previously described in connection with the first embodiment to effect low-temperature cooking. In practice, the food load may be in a bag or in any covered or uncovered form.

The term "no-flow intervals," as used herein, is intended to cover intervals between the hot-air pulses which flow at high velocity in which flow is either fully interrupted or in which the velocity of flow is substantially reduced.

While there have been shown and described preferred embodiments of a countor-top oven in accordance with the invention, it will be appreciated that many changes and modifications may be made therein without, however, departing from the essential spirit thereof. Thus the shelf 17 may have a diamond-like rather than a corrugated pattern, the invention covering any configuration which defines peaks to support the food and depressions having holes therein to admit hot air into the food compartment. Also, since the oven is used for cooking as well as rethermalizing, the hot air circulated therein will pick up grease, smoke and other volatile constituents; hence in practice, a replaceable or disposable filter is preferably interposed in the flow path to extract these constituents. And while electrical heaters are shown to generate the required oven heat, gas and other heat-producing energy sources may be used.

In order to be able to brown food such as chicken without having to turn the food in rotisserie fashion within the oven to ensure even browning thereof, the side walls of the oven as well as the shelf are preferably in the form of metal panels having diamond-shaped indentations therein. These indentations act as corner reflectors and serve to reflect the infrared rays in multiple directions. Thus the rays coming directly from the infrared heaters as well as those reflected by the shelf and the side walls act to irradiate all surfaces of the food with infrared energy to effect uniform browning thereof. Also, while the drip pan below the shelf serves to pick up grease, by filling it with water, the pan then functions to humidify the atmosphere; for the water vapor picked up by the circulating hot air acts to prevent the food being cooked from drying out.

I claim:

1. A counter-top oven adapted to effect low-temperature cooking of food having a predetermined cooking temperature at a relatively rapid rate whereby nutrients and other valuable food constituents are preserved, said oven comprising:

A. A food-receiving compartment having a perforated bottom wall and a top wall provided with a port, said compartment being supported within a case and being spaced therefrom to create air spaces therebetween;

B. means external to said compartment to heat air to a high temperature level well above said cooking temperature and to force the hot air through the perforations in said bottom wall at high pressure to produce a high velocity flow of hot air through the compartment in heat exchange relation with the food therein, the hot air being discharged from the compartment through the port, said means being constituted by a motor-driven fan in one of said air spaces arranged to draw air from said compartment through said top wall port to produce a negative pressure in said compartment and a positive pressure in the air spaces, the resultant pressure differential forcing air through said perforations; and C. means periodically to interrupt the flow of hot air to generate within the compartment hot air pulses having no-flow intervals therebetween in a manner creating a laminar heat transfer pattern wherein heat acquired by the outer layer of the body of food in the compartment is transferred in these intervals to the intermediate layers and core of the body, causing the outer layer to go down in temperature during these intervals to a degree preventing the temperature of the outer layer from ever rising substantially above the cooking temperature despite the much higher temperature of the hot air pulses in heat exchange relation therewith.

2. An oven as set forth in claim 1, wherein the air space containing the motor also has an electrical resistance heater therein to heat the air drawn from the compartment to said high temperature level.

3. An oven as set forth in claim 2, further including means to periodically energize said heater and said motor to provide said interruptions in air flow.

4. An oven as set forth in claim 1, wherein perforated wall is constituted by a slidable shelf on which said food rests.

5. An oven as set forth in claim 4, wherein said shelf is of corrugated construction with holes in the troughs thereof.

6. An oven as set forth in claim 1, wherein said compartment in said case has an open front, and said case has a hinged door which, when shut, closes said open front.

7. An oven as set forth in claim 1, further including a bank of quartz heaters in said compartment disposed above the food therein, and means to sequentially actuate said quartz heaters to cause the radiation thereof to sweep across the surface of the food to brown same.

8. An oven as set forth in claim 7, wherein each quartz heater is formed by a heater element disposed within a reflector.

9. An oven as set forth in claim 1, wherein the walls of said case are thermally-insulated.

10. An oven as set forth in claim 1, further including a filter interposed in the flow path of hot air through said compartment.

*11. An oven adapted to cook a food product having a predetermined cooking temperature at which its nutrients and other valuable constituents are substantially preserved whereby cooking well above this temperature would have an adverse effect on the product, the oven comprising:*

*A. a compartment for receiving the food product to be cooked;*

*B. means external to said compartment to heat air to a temperature well above said predetermined temperature to produce hot air;*

*C. means to cause said hot air to flow through said compartment at high velocity in heat exchange relationship with said food product; and*

*D. means periodically to interrupt said flow of hot air to generate within the compartment hot air pulses having substantially-reduced flow intervals therebetween in a manner creating a pulsatory heat transfer pattern wherein heat acquired from the pulses by the outer layer of the body of the food product is transferred inwardly in the intervals between pulses to the intermediate layers and core of the body to cause the outer layer to go down in temperature during these intervals to a degree preventing the temperature of the outer layer from ever rising substantially above the predetermined cooking temperature despite the higher temperature of the hot air pulses in heat exchange relationship therewith.*

*12. An oven as set forth in claim 11, wherein said means to heat air is constituted by an electrical heating element.*

*13. An oven as set forth in claim 12, wherein said means to cause said hot air to flow through said compartment at high velocity is constituted by a blower which blows air across said heating element.*

*14. An oven as set forth in claim 13, wherein said means periodically to interrupt the flow of hot air is constituted by means to periodically energize said heating element.*

*15. An oven as set forth in claim 13, wherein said means periodically to interrupt the flow of hot air is constituted by means to periodically block the flow of said hot air.*

* * * * *